United States Patent
Lai et al.

(10) Patent No.: US 10,968,447 B2
(45) Date of Patent: Apr. 6, 2021

(54) METHODS AND COMPOSITIONS FOR ENRICHMENT OF TARGET POLYNUCLEOTIDES

(71) Applicant: MYRIAD WOMEN'S HEALTH, INC., South San Francisco, CA (US)

(72) Inventors: Henry H. Lai, San Francisco, CA (US); Clement S. Chu, San Francisco, CA (US)

(73) Assignee: MYRIAD WOMEN'S HEALTH, INC., South San Francisco, CA (US)

(*) Notice: Subject to any disclaimer, the term of this patent is extended or adjusted under 35 U.S.C. 154(b) by 366 days.

(21) Appl. No.: 15/873,667

(22) Filed: Jan. 17, 2018

(65) Prior Publication Data

US 2018/0216103 A1    Aug. 2, 2018

Related U.S. Application Data

(60) Provisional application No. 62/452,875, filed on Jan. 31, 2017.

(51) Int. Cl.
| | | |
|---|---|---|
| *C12N 15/10* | (2006.01) | |
| *C12Q 1/68* | (2018.01) | |
| *C12Q 1/6806* | (2018.01) | |
| *C12Q 1/686* | (2018.01) | |
| *C12Q 1/6855* | (2018.01) | |

(52) U.S. Cl.
CPC ....... *C12N 15/1093* (2013.01); *C12Q 1/6806* (2013.01); *C12Q 1/686* (2013.01); *C12Q 1/6855* (2013.01); *C12Q 2600/112* (2013.01); *C12Q 2600/124* (2013.01)

(58) Field of Classification Search
CPC .................................................. C12Q 1/6855
See application file for complete search history.

(56) References Cited

U.S. PATENT DOCUMENTS

| | | | |
|---|---|---|---|
| 5,476,930 A | 12/1995 | Letsinger et al. | |
| 5,780,613 A | 7/1998 | Letsinger et al. | |
| 7,115,400 B1 | 10/2006 | Adessi et al. | |
| 8,383,338 B2 | 2/2013 | Kitzman et al. | |
| 9,092,401 B2 | 7/2015 | Richards et al. | |
| 9,309,556 B2 | 4/2016 | Myllykangas et al. | |
| 10,752,946 B2 * | 8/2020 | Chu ..................... | C12Q 1/6809 |
| 2008/0160580 A1 | 7/2008 | Adessi et al. | |
| 2008/0286795 A1 | 11/2008 | Kawashima et al. | |
| 2010/0022406 A1 | 1/2010 | Srinivasan et al. | |
| 2012/0295819 A1 | 11/2012 | Leamon et al. | |
| 2013/0171185 A1 | 7/2013 | Settembre et al. | |
| 2014/0024536 A1 | 1/2014 | Richards et al. | |
| 2014/0024541 A1 | 1/2014 | Richards et al. | |
| 2014/0121116 A1 | 5/2014 | Richards et al. | |
| 2014/0141982 A1 | 5/2014 | Jacobson et al. | |
| 2014/0162278 A1 | 6/2014 | Richards et al. | |
| 2014/0274740 A1 | 9/2014 | Srinivasan et al. | |
| 2015/0017635 A1 | 1/2015 | Myllykangas et al. | |
| 2015/0044687 A1 | 2/2015 | Schmitt et al. | |
| 2015/0205914 A1 | 7/2015 | Richards et al. | |
| 2015/0275289 A1 | 10/2015 | Otwinowski et al. | |
| 2015/0284712 A1 * | 10/2015 | Kurihara ............ | C12N 15/1065 506/26 |
| 2015/0353926 A1 | 12/2015 | Rigatti et al. | |
| 2016/0068903 A1 | 3/2016 | Zhou et al. | |
| 2016/0115544 A1 | 4/2016 | Elzinga et al. | |
| 2016/0319345 A1 * | 11/2016 | Gnerre ................. | C12Q 1/6855 |
| 2017/0321270 A1 | 11/2017 | Hague et al. | |
| 2017/0355984 A1 | 12/2017 | Evans et al. | |
| 2018/0089364 A1 | 3/2018 | Muzzey et al. | |
| 2018/0201994 A1 | 7/2018 | Beauchamp et al. | |
| 2018/1216176 | 8/2018 | Chu et al. | |

FOREIGN PATENT DOCUMENTS

| | | | |
|---|---|---|---|
| WO | WO2010/151842 A2 | 12/2010 | |
| WO | WO2012003374 A2 | 1/2012 | |
| WO | WO2012040387 A1 | 3/2012 | |
| WO | WO2013112923 A1 | 8/2013 | |
| WO | WO-2014144495 A1 * | 9/2014 | .......... C12Q 1/6809 |
| WO | WO2016/010856 A1 | 1/2016 | |
| WO | WO2016130704 A2 | 8/2016 | |
| WO | WO2018144216 A1 | 8/2018 | |

(Continued)

OTHER PUBLICATIONS

Kircher M, Sawyer S, Meyer M. Double indexing overcomes inaccuracies in multiplex sequencing on the Illumina platform. Nucleic acids research. Jan. 1, 2012; 40(1):e3 pp. 1-8. (Year: 2012).*

Kircher et al. Supplementary pp. 1-17. Nucleic acids research. Jan. 1, 2012; 40(1):e3 pp. 1-8. (Year: 2012).*

Knapp M, Stiller M, Meyer M. Generating barcoded libraries for multiplex high-throughput sequencing. Methods Mol Biol. 2012; 840: 155-170. (Year: 2012).*

Kozich et al. Development of a dual-index sequencing strategy and curation pipeline for analyzing amplicon sequence data on the MiSeq Illumina sequencing platform. Appl. Environ. Microbiol. Sep. 1, 2013; 79(17):5112-20. (Year: 2013).*

Lovett ST. The DNA Exonucleases of *Escherichia coli*. EcoSal Plus. Dec. 2011 ; 4(2):10 p. 1-45. (Year: 2011).*

(Continued)

*Primary Examiner* — Teresa E Strzelecka
*Assistant Examiner* — Olayinka A Oyeyemi
(74) *Attorney, Agent, or Firm* — FisherBroyles, LLP; Jill A. Jacobson; Victorial Brewster (57) ABSTRACT

High-fidelity, high-throughput nucleic acid sequencing enables healthcare practitioners and patients to gain insight into genetic variants and potential health risks. However, previous methods of nucleic acid sequencing often introduces sequencing errors (for example, mutations that arise during the preparation of a nucleic acid library, during amplification, or sequencing). Provided herein are methods and compositions for sequencing nucleic acids. Further provided are methods of identifying an error in a nucleic acid sequence.

26 Claims, 2 Drawing Sheets

(56) References Cited

FOREIGN PATENT DOCUMENTS

WO 2018/161019 A1 9/2018

OTHER PUBLICATIONS

Meyer M, Kircher M. Illumina sequencing library preparation for highly multiplexed target capture and sequencing. Cold Spring Harbor Protocols. Jun. 1, 2010; 2010(6): 1-20. (Year: 2010).*

Murgha, Yusuf Esmail. Large-Scale Generation of Synthetic DNA Libraries: Sequence-Specific Priming of Reverse Transcription. PhD diss., 2012. (Year: 2012).*

Nikiforov TT, Rendle RB, Kotewicz ML, Rogers YH. The use of phosphorothioate primers and exonuclease hydrolysis for the preparation of single-stranded PCR products and their detection by solid-phase hybridization. Genome Research. Apr. 1, 1994; 3(5): 285-91. (Year: 1994).*

Peng Q, Satya RV, Lewis M, Randad P, Wang Y. Reducing amplification artifacts in high multiplex amplicon sequencing by using molecular barcodes. BMC genomics. Dec. 2015; 16(1):589 pp. 1-12. (Year: 2015).*

Horhota, A., et al., Glycerol Nucleoside Triphosphates: Synthesis and Polymerase Substrate Activities, Organic Letters, 2006, 8(23):5345-5347.

Altshul, S., et al., Basic Local Alignment Search Tool, J. Mol. Biol., 1990, 215:403-410.

Henikoff, S., et al., Amino acid substitution matrices from protein blocks, Proc. Natl. Acad. Sof, 1992, 89:10915-10919.

Karlin, S., et al., Applications and statistics for multiple high-scoring segments in molecular sequences, Proc. Natl. Acad. Sci., 1993, 90:5873-5877.

Higgins, D.G., et al., CLUSTAL: a package for performing multiple sequence alignment on a microcomputer, Gene, 1998, 73:237-244.

Pearson, W.R., et al., Improved tools for biological sequence comparison, Proc. Natl. Acad. Sci., 1988, 85:2444-2448.

Alnemri, E.S., et al., Activation of Internucleosomal DNA Cleavage in Human CEM Lymphcytes by Glucocorticoid and Novobiocin, J. Biol. Chem., 1990, 265(28):17323-17333.

Richards, O.C., et al., Chemical Mechanism of Sonic, Acid, Alkaline and Enzymic Degradation of DNA, J. Mol. Biol., 1965, 11:327-340.

NimbleGen Seq EZ Library SR Users Guide, Roche, 2014.

Hybridization capture of DNA libraries using xGen Lockdown Probes and Reagents, IDT Integrated DNA Technologies 2015.

Ahn, J., et al., Asymmetrical barcode adapter-assisted recovery of duplicate reads and error correction strategy to detect rare mutations in circulating tumor DNA, Scientific Reports, May 2, 2017, 7(46678): 1-9.

Hopmans, E., et al., A programmable method for massively parallel targeted sequencing, Nucleic Acids Research 42 (10):e88, Apr. 29, 2014.

Zhong, S., et al., High-Throughput Illumina Strand-Specific RNA Sequencing Library Preparation, Cold Sptring Harb Protoc 2011(8):940-949, 2011.

Mertes, E et al., Targeted Enrichment of Genomic DNA Regions for Next-Generation Sequencing, Briefings in Functional Genomics 10(6):374-386, Nov. 26, 2011.

Myllykangas, S., et al., Efficient Targeted Resequencing of Human Germline and Cancer Genomes by Oligonucleotide-Selective Sequencing, Nat Biotechnol 29(11):1024-1027, Oct. 23, 2011.

NG, S.B., et al., Targeted Capture and Massively Parallel Sequencing of Twelve Human Exomes, Nature 461 (7261):272-276, Aug. 16, 2009.

Gundmundsson, J., et al., Genome-wide association and replication studies identify four variants associated with prostate cancer susceptibility, Nat Genet 41:1122-1126, 2009.

Illumina, Quality Scores for Next Generation Sequencing, Pub. No., 770-2011-030, Oct. 31, 2011.

Illumina, Understanding Illumina Quality Scores, Pub. No. 770-2012-058, Apr. 23, 2014.

Illumina, Calculating Percent Passing Filter for Patterned and Nonpatterned Flow Cells, Pub. No. 770-2014-043-B, 2017.

Samorodnitsky, E., et al., Comparison of custom capture for targeted next-generation DNA sequencing, J Mol Diagn 17:64-75, Jan. 15, 2015.

Turner, E., et al., Massively parallel exon capture and library-free resequencing across 16 genomes, Nat. Methods 6:315-316, 2009.

* cited by examiner

FIGURE 1

METHODS AND COMPOSITIONS FOR ENRICHMENT OF TARGET POLYNUCLEOTIDES

CROSS-REFERENCE TO RELATED APPLICATIONS

This application claims the benefit of U.S. Provisional Application No. 62/452,875, filed on Jan. 31, 2017, which is incorporated herein by reference in its entirety.

FIELD OF THE INVENTION

The present invention relates to methods and compositions for sequencing nucleic acids.

BACKGROUND

Next-generation sequencing (NGS) allows small-scale, inexpensive genome sequencing with a turnaround time measured in days. However, as NGS is generally performed and understood, all regions are sequenced with roughly equal probability, meaning that a large amount of genomic sequence is collected and discarded to collect sequence information from the relatively low percentage of areas where function is understood well enough to interpret potential mutations. Generally, purifying from a full-genome sample only those regions one is interested in is conducted as a separate step from sequencing. It is usually a days-long, low efficiency process in the current state of the art.

Next generation sequencing of nucleic acids has greatly increased the rate of genomic sequencing, thereby bringing in a new era for medical diagnostics, forensics, metagenomics, and many other applications. However, these high-throughput approaches often incorporate errors, resulting in inaccuracies in a constructed consensus sequence. These errors can arise, for example, during nucleic acid amplification or sequencing, or downstream analysis. Additionally, errors can arise due to chemical damage of the original nucleic acid molecule. In some cases, as many as 1% of sequenced bases can be incorrectly identified. These errors in the nucleic acid consensus sequence limit the reliability of known NGS methods.

Direct Targeted Sequencing (DTS) is a modification to the standard sequencing protocol employed by Illumina, Inc. that allows the sequencing substrate (i.e., the flow cell) to become a genomic sequence capture substrate as well. Without adding another instrument to the normal flow of a typical NGS protocol, the DTS protocol modifies the sequencing surface to capture genomic DNA (gDNA) from a specially prepared library. The captured library is then sequenced as a normal gDNA library would be. However, modification of the sequencing substrate and accompanying library preparation according to previous suggestions result in inefficiencies, reduced reliability and reproducibility, and waste valuable sample. Improvements to the DTS process are therefore desirable.

BRIEF SUMMARY OF THE INVENTION

Methods and compositions are provided for preparing and sequencing target nucleic acids.

In one aspect, methods are provided for preparing a target nucleic acid duplex molecule for sequencing. In some embodiments, the methods include:

(a) ligating an adaptor to each end of a target nucleic acid duplex, wherein the target nucleic acid duplex includes first and second nucleic acid strands that are complementary to one another, wherein each of said adaptors includes: (i) a double stranded region that is ligated to one end of the target nucleic acid duplex; and (ii) first and second single stranded regions, wherein the first single stranded region includes an amplification primer binding sequence S2 and a 3' end, and wherein the second single stranded region includes, from 5' to 3', a 5' end, a first grafting sequence P5 for attachment to a flow cell, a first sample index sequence SI5, a molecular barcode A, and a first sequencing primer binding site S1, or wherein the second single stranded region includes, from 5' to 3', a 5' end, a first grafting sequence P5 for attachment to a flow cell, a molecular barcode A, a first sample index sequence SI5, and a first sequencing primer binding site S1, wherein the molecular barcodes on the adaptors are the same or different;

(b) amplifying the ligated nucleic acid produced in (a) using a first amplification primer that includes a nucleic acid sequence that is complementary to the amplification primer binding sequence S2 and a second amplification primer that is complementary to at least a portion of the first grafting sequence P5, wherein the first amplification primer includes a 5' phosphate group, and wherein the second amplification primer includes one or more nucleotide(s) at or near the 5' end that includes a modification to prevent nucleic acid strand degradation by an exonuclease enzyme;

(c) digesting the amplified nucleic acids produced in (b) with a 5'→3' exonuclease, thereby yielding single stranded nucleic acid products that include the sequence of either the first or second strand of the target nucleic acid duplex and the modified nucleotide(s) at and/or near the 5' end;

(d) hybridizing and extending a primer that comprises: (i) a probe sequence that is complementary to a portion of the target nucleic acid sequence of the first or second strand; and (ii) a second sequencing primer binding sequence S3, thereby producing primer extension products that comprise the first grafting sequence P5 at the 3' end and second sequencing primer binding sequence S3 at the 5' end; and (e) amplifying the primer extension products, using: (i) a third amplification primer that comprises, from 5' to 3', a second grafting sequence P7, a second sample index sequence SI7, and a sequence that is complementary to the second sequencing binding sequence S3; and (ii) a fourth amplification primer that comprises a sequence that is complementary to the first grafting sequence P5, thereby producing amplified primer extension products and their complements for sequencing.

In some embodiments, the starting material for the method includes about 1 ng, about 5 ng, or about 15 ng or more of fragmented DNA. In some embodiments, the molecular barcode in the second single-stranded region of the adaptor is about 5 to about 15 nucleotides in length.

In some embodiments, the target nucleic acid duplex includes cell-free DNA, for example, but not limited to, cell-free tumor DNA or cell-free fetal DNA. In some embodiments, the target nucleic acid duplex is enriched from a nucleic acid library, for example, but not limited to, enrichment using a set of capture probes for a region of interest.

In some embodiments, amplifying the ligated nucleic acid (e.g., in step (b)) includes polymerase chain reaction (PCR) or a linear amplification method. In some embodiments, the amplified ligated nucleic acid product (e.g., in step (b)) includes about 200 ng or more of amplified ligated nucleic acid.

In some embodiments, the modified nucleotide(s) in the second amplification primer (e.g., in step (b)) include a 5' phosphorothioate group. In some embodiments, the second amplification primer includes five or more phosphorothioate modified nucleotides at or near the 5' end of the primer.

In some embodiments, the exonuclease (e.g., in step (c)) is a double-stranded exonuclease. In one embodiment, the exonuclease is a lambda exonuclease.

In some embodiments, the method includes repeating the primer extension (e.g., step (d)) with a plurality of different probes, in different reaction mixtures, to produce a plurality of primer extension products that will provide different start points for sequencing of the target nucleic acid sequence.

In some embodiments, amplifying the primer extension products (e.g., in step (e)) includes PCR or a linear amplification method.

In another aspect, methods are provided for sequencing a target nucleic acid. The methods include preparing a target nucleic acid duplex for sequencing according to a method as described herein and sequencing the product produced thereto (e.g., sequencing the product of step (e) as described above).

In some embodiments, nucleic acid sequencing occurs in a flow cell, e.g., a flow cell that includes oligonucleotides that are complementary to and to which the first and/or second grafting sequence hybridizes.

In some embodiments, a first read is performed to read the first strand target sequence on the amplified primer extension product that includes the first strand target sequence, using a primer with a sequence that is complementary to the first sequencing primer binding site. In some embodiments, a second read is performed to read the second sample index sequence on the amplified primer extension product that includes the first strand target sequence. In some embodiments, a third read is performed to read the molecular barcode and first sample index sequences on the amplified primer extension product that includes the complement of the first strand target sequence. In some embodiments, a fourth read is performed to read the probe sequence and the sequence that is complementary to the first strand target sequence on the amplified primer extension product that includes the complement of the first strand target sequence, using a primer with a sequence that is complementary to the second sequencing primer binding sequence.

In some embodiments, a set of first reads is compiled to construct a consensus sequence of the first strand of the target nucleic acid duplex. For example, the set of first strand reads is compiled based on sequence distance or alignment to a reference sequence. In some embodiments, constructing the first strand consensus sequence includes: comparing the first strand reads in the set of first strand reads; identifying and removing errors in the set of first strand reads; and constructing an error-corrected first strand consensus sequence. In some embodiments, a mutation is identified by comparison of the error-corrected consensus sequence to a reference sequence.

In another aspect, methods are provided for preparing a nucleic acid sequencing library. The methods include preparing a plurality of target DNA duplexes for sequencing in accordance with any of the methods described herein. For example, the nucleic acid sequencing library includes a plurality of amplified primer extension products, e.g., the products of step (e) above.

DETAILED DESCRIPTION

The invention provides compositions and methods for preparing and sequencing nucleic acids. Among the advantages of the methods described herein are the ability to sequence a desired target sequence using a very low input of nucleic acid and the ability to sequence a specific target strand of interest. A library amplification step is included, which permits a lower input quantity of nucleic acid than other methods in the art. Further, an exonuclease digestion of the complement of an amplified target nucleic acid strand is performed, permitting sequencing of the starting nucleic acid strand specifically. The methods described herein have reduced complexity in comparison to other sequencing methods, including the presence of only one molecular barcode on the nucleic acid construct that is sequenced. Further, the methods described herein do not require additional modifications for a selection event, such as, for example, biotin/streptavidin.

Definitions

Numeric ranges are inclusive of the numbers defining the range.

The term "about" is used herein to mean plus or minus ten percent (10%) of a value. For example, "about 100" refers to any number between 90 and 110.

"A," "an" and "the" include plural references unless the context clearly dictates otherwise.

The term "adaptor" herein refers to a nucleic acid that is attached to both strands of a double-stranded DNA molecule. The adaptor can be composed of two distinct oligonucleotide molecules that are base-paired with one another, i.e., complementary. Alternatively, the adaptor can be composed of a single oligonucleotide that includes one or more regions of complementarity, and one or more non-complementary regions.

In general, as used herein, a sequence element located "at the 3' end" includes the 3'-most nucleotide of the oligonucleotide, and a sequence element located "at the 5' end" includes the 5'-most nucleotide of the oligonucleotide.

As used herein, the term "barcode" or "molecular barcode" (also termed single molecule identifier (SMI)) refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are about or at least about 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some polynucleotides are of different lengths than barcodes associated with other polynucleotides. In general, barcodes are of sufficient length and include sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differ from every other barcode in the plurality at least three nucleotide positions, such as at least 3, 4, 5, 6, 7, 8, 9, 10, or more nucleotide positions. A plurality of barcodes may be represented in a pool of samples, each sample including polynucleotides comprising one or more barcodes that differ from the barcodes contained in the polynucleotides derived from the other samples in the pool. Samples of polynucleotides including one or more barcodes can be pooled based on the barcode sequences to which they are joined, such that all four of the nucleotide bases A, G, C, and T are approximately evenly represented at one or more positions along each barcode in the pool (such as at 1, 2, 3, 4, 5, 6, 7, 8, or more positions, or all positions of the barcode).

A "blocking group" is any modification that prevents extension of a 3' end of an oligonucleotide, such as by a polymerase, a ligase, and/or other enzymes.

The term "base pair" or "bp" as used herein refers to a partnership (i.e., hydrogen bonded pairing) of adenine (A) with thymine (T), or of cytosine (C) with guanine (G) in a double stranded DNA molecule. In some embodiments, a base pair may include A paired with Uracil (U), for example, in a DNA/RNA duplex.

A "causal genetic variant" is a genetic variant for which there is statistical, biological, and/or functional evidence of association with a disease or trait.

In general, a "complement" of a given nucleic acid sequence is a sequence that is fully complementary to and hybridizable to the given sequence. In general, a first sequence that is hybridizable to a second sequence or set of second sequences is specifically or selectively hybridizable to the second sequence or set of second sequences, such that hybridization to the second sequence or set of second sequences is preferred (e.g., thermodynamically more stable under a given set of conditions, such as stringent conditions commonly used in the art) in comparison with hybridization with non-target sequences during a hybridization reaction. Typically, hybridizable sequences share a degree of sequence complementarity over all or a portion of their respective lengths, such as 25%-100% complementarity, including at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

The term "complementary" herein refers to the broad concept of sequence complementarity in duplex regions of a single polynucleotide strand or between two polynucleotide strands between pairs of nucleotides through base-pairing. It is known that an adenine nucleotide is capable of forming specific hydrogen bonds ("base pairing") with a nucleotide, which is thymine or uracil. Similarly, it is known that a cytosine nucleotide is capable of base pairing with a guanine nucleotide. However, in certain circumstances, hydrogen bonds may also form between other pairs of bases, e.g., between adenine and cytosine, etc. "Essentially complementary" herein refers to sequence complementarity in duplex regions of a single polynucleotide strand or between two polynucleotide strands, for example, wherein the complementarity is less than 100% but is greater than 90%, and retains the stability of the duplex region.

The term "derived from" encompasses the terms "originated from," "obtained from," "obtainable from," "isolated from," and "created from," and generally indicates that one specified material finds its origin in another specified material or has features that can be described with reference to the another specified material.

The term "duplex" herein refers to a region of complementarity that exists between two polynucleotide sequences.

The term "duplex region" refers to the region of sequence complementarity that exists between two oligonucleotides or two portions of a single oligonucleotide.

The term "end-repaired DNA" herein refers to DNA that has been subjected to enzymatic reactions in vitro to bluntend 5'- and/or 3'-overhangs. Blunt ends can be obtained by filling in missing bases for a strand in the 5' to 3' direction using a polymerase, and by removing 3'-overhangs using an exonuclease. For example, T4 polymerase and/or Klenow DNA polymerase may be used for DNA end repair.

The terms "first end" and "second end" when used in reference to a nucleic acid molecule, herein refers to ends of a linear nucleic acid molecule.

A "gene" refers to a DNA segment that is involved in producing a polypeptide and includes regions preceding and following the coding regions as well as intervening sequences (introns) between individual coding segments (exons).

"Hybridization" and "annealing" refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may include two nucleic acid strands forming a duplex structure, three or more strands forming a multi-stranded complex, a single self-hybridizing strand, or any combination of these. A hybridization reaction may constitute a step in a more extensive process, such as the initiation of polymerase chain reaction (PCR), ligation reaction, sequencing reaction, or cleavage reaction, e.g., enzymatic cleavage of a polynucleotide by a ribozyme. A first nucleic acid sequence that can be stabilized via hydrogen bonding with the bases of the nucleotide residues of a second sequence is said to be "hybridizable" to the second sequence. In such a case, the second sequence can also be said to be hybridizable to the first sequence. The term "hybridized" refers to a polynucleotide in a complex that is stabilized via hydrogen bonding between the bases of the nucleotide residues.

When referring to immobilization or attachment of molecules (e.g., nucleic acids) to a solid support, the terms "immobilized" and "attached" are used interchangeably herein, and both terms are intended to encompass direct or indirect, covalent or non-covalent attachment, unless indicated otherwise. In some embodiments, covalent attachment may be preferred, but generally all that is required is that the molecules (e.g., nucleic acids) remain immobilized or attached to the support under the conditions in which it is intended to use the support, for example in nucleic acid amplification and/or sequencing applications.

The terms "isolated," "purified," "separated," and "recovered" as used herein refer to a material (e.g., a protein, nucleic acid, or cell) that is removed from at least one component with which it is naturally associated, for example, at a concentration of at least 90% by weight, or at least 95% by weight, or at least 98% by weight of the sample in which it is contained. For example, these terms may refer to a material which is substantially or essentially free from components which normally accompany it as found in its native state, such as, for example, an intact biological system. An isolated nucleic acid molecule includes a nucleic acid molecule contained in cells that ordinarily express the nucleic acid molecule, but the nucleic acid molecule is present extrachromosomally or at a chromosomal location that is different from its natural chromosomal location.

The terms "joining" and "ligation" as used herein, with respect to two polynucleotides, such as an adapter oligonucleotide and a sample polynucleotide, refers to the covalent attachment of two separate polynucleotides to produce a single larger polynucleotide with a contiguous backbone.

The term "library" herein refers to a collection or plurality of template molecules, i.e., target DNA duplexes, which share common sequences at their 5' ends and common sequences at their 3' ends. Use of the term "library" to refer to a collection or plurality of template molecules should not be taken to imply that the templates making up the library are derived from a particular source, or that the "library" has a particular composition. By way of example, use of the term "library" should not be taken to imply that the individual templates within the library must be of different nucleotide sequence or that the templates must be related in terms of sequence and/or source.

The term "mutation" herein refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

The term "Next Generation Sequencing (NGS)" herein refers to sequencing methods that allow for massively parallel sequencing of clonally amplified and of single nucleic acid molecules during which a plurality, e.g., millions, of nucleic acid fragments from a single sample or from multiple different samples are sequenced in unison. Non-limiting examples of NGS include sequencing-by-synthesis, sequencing-by-ligation, real-time sequencing, and nanopore sequencing.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of polymeric operatively linked nucleotides is typically referred to herein as a "base sequence" or "nucleotide sequence," or nucleic acid or polynucleotide "strand," and is represented herein by a formula whose left to right orientation is in the conventional direction of 5'-terminus to 3'-terminus, referring to the terminal 5' phosphate group and the terminal 3' hydroxyl group at the "5'" and "3'" ends of the polymeric sequence, respectively.

The term "nucleotide analog" herein refers to analogs of nucleoside triphosphates, e.g., (S)-Glycerol nucleoside triphosphates (gNTPs) of the common nucleobases: adenine, cytosine, guanine, uracil, and thymidine (Horhota et al., *Organic Letters*, 8:5345-5347 [2006]). Also encompassed are nucleoside tetraphosphate, nucleoside pentaphosphates and nucleoside hexaphosphates.

The term "operably linked" refers to a juxtaposition or arrangement of specified elements that allows them to perform in concert to bring about an effect. For example, a promoter is operably linked to a coding sequence if it controls the transcription of the coding sequence.

The term "polymerase" herein refers to an enzyme that catalyzes the polymerization of nucleotides (i.e., the polymerase activity). The term polymerase encompasses DNA polymerases, RNA polymerases, and reverse transcriptases. A "DNA polymerase" catalyzes the polymerization of deoxyribonucleotides. An "RNA polymerase" catalyzes the polymerization of ribonucleotides. A "reverse transcriptase" catalyzes the polymerization of deoxyribonucleotides that are complementary to an RNA template.

The terms "polynucleotide," "nucleotide," "nucleotide sequence," "nucleic acid," and "oligonucleotide" are used interchangeably. They refer to a oligomeric form of nucleotides of any length, either deoxyribonucleotides or ribonucleotides, or analogs thereof. Polynucleotides may have any three-dimensional structure, and may perform any function, known or unknown. and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need and circular portions. The following are nonlimiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adapters, and primers. A polynucleotide may include modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component, tag, reactive moiety, or binding partner. Polynucleotide sequences, when provided, are listed in the 5' to 3' direction, unless stated otherwise.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may include modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The term "primer" herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and a polymerase enzyme, e.g., a thermostable enzyme, in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the polymerase, e.g., thermostable polymerase enzyme. The exact lengths of a primer will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

A "promoter" refers to a regulatory sequence that is involved in binding RNA polymerase to initiate transcription of a gene. A promoter may be an inducible promoter or a constitutive promoter. An "inducible promoter" is a promoter that is active under environmental or developmental regulatory conditions.

A "sample index" or "index" sequence refers to a predefined known sequence, for example, 6-12 nucleotides in length.

The term "sequencing library" herein refers to DNA that is processed for sequencing, e.g., using massively parallel methods, e.g., NGS. The DNA may optionally be amplified to obtain a population of multiple copies of processed DNA, which can be sequenced by NGS.

The term "single stranded overhang" or "overhang" is used herein to refer to a strand of a double stranded (ds) nucleic acid molecule that extends beyond the terminus of the complementary strand of the ds nucleic acid molecule. The term "5' overhang" or "5' overhanging sequence" is used herein to refer to a strand of a ds nucleic acid molecule that extends in a 5' direction beyond the 3' terminus of the complementary strand of the ds nucleic acid molecule. The term "3' overhang" or "3' overhanging sequence" is used herein to refer to a strand of a ds nucleic acid molecule that extends in a 3' direction beyond the 5' terminus of the complementary strand of the ds nucleic acid molecule.

A "spacer" may consist of a repeated single nucleotide (e.g., 1, 2, 3, 4, 5, 6, 7, 8, 9, 10, or more of the same nucleotide in a row), or a sequence of 2, 3, 4, 5, 6, 7, 8, 9, 10, or more nucleotides repeated 1, 2, 3, 4, 5, 6, 7, 8, 9, 10, or more times. A spacer may comprise or consist of a specific sequence, such as a sequence that does not hybridize to any target sequence in a sample. A spacer may comprise or consist of a sequence of randomly selected nucleotides.

The phrases "substantially similar" and "substantially identical" in the context of at least two nucleic acids typically means that a polynucleotide includes a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical nucleic acid molecules hybridize to each other under stringent conditions (e.g., within a range of medium to high stringency).

Nucleic acid "synthesis" herein refers to any in vitro method for making a new strand of polynucleotide or elongating an existing polynucleotide (i.e., DNA or RNA) in a template dependent manner. Synthesis, according to the invention, can include amplification, which increases the number of copies of a polynucleotide template sequence with the use of a polymerase. Polynucleotide synthesis (e.g., amplification) results in the incorporation of nucleotides into a polynucleotide (e.g., extension from a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, polymerase chain reaction (PCR), and may include the use of labeled nucleotides, e.g., for probes and oligonucleotide primers, or for polynucleotide sequencing.

The term "tag" refers to a detectable moiety that may be one or more atom(s) or molecule(s), or a collection of atoms and molecules. A tag may provide an optical, electrochemical, magnetic, or electrostatic (e.g., inductive, capacitive) signature.

The term "tagged nucleotide" herein refers to a nucleotide that includes a tag (or tag species) that is coupled to any location of the nucleotide including, but not limited to a phosphate (e.g., terminal phosphate), sugar or nitrogenous base moiety of the nucleotide. Tags may be one or more atom(s) or molecule(s), or a collection of atoms and molecules. A tag may provide an optical, electrochemical, magnetic, or electrostatic (e.g., inductive, capacitive) signature.

The term "target DNA duplex" herein refers to a double stranded DNA molecule that is derived from a sample polynucleotide that is DNA, e.g., genomic or cell-free DNA ("cfDNA"), and/or RNA.

As used herein, the term "target polynucleotide" refers to a nucleic acid molecule or polynucleotide in a population of nucleic acid molecules having a target sequence to which one or more oligonucleotides are designed to hybridize. In some embodiments, a target sequence uniquely identifies a sequence derived from a sample, such as a particular genomic, mitochondrial, bacterial, viral, or RNA (e.g., mRNA, miRNA, primary miRNA, or pre-miRNA) sequence. In some embodiments, a target sequence is a common sequence shared by multiple different target polynucleotides, such as a common adapter sequence joined to different target polynucleotides. "Target polynucleotide" may be used to refer to a double-stranded nucleic acid molecule that includes a target sequence on one or both strands, or a single-stranded nucleic acid molecule including a target sequence, and may be derived from any source of or process for isolating or generating nucleic acid molecules. A target polynucleotide may include one or more (e.g., 1, 2, 3, 4, 5, 6, 7, 8, 9, 10, or more) target sequences, which may be the same or different. In general, different target polynucleotides include different sequences, such as one or more different nucleotides or one or more different target sequences.

The term "template DNA molecule" herein refers to a strand of a nucleic acid from which a complementary nucleic acid strand is synthesized by a DNA polymerase, for example, in a primer extension reaction.

The term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene*, 4th Ed., W. A. Benjamin, Inc., Menlo Park, Calif. (1987)).

Target Nucleic Acids

Target nucleic acid duplex molecules are provided, and prepared for sequencing in methods provided herein. The target nucleic acid duplex may be derived from a source in which the target exists as double-stranded DNA, such as genomic DNA, or it may be prepared from a single-stranded nucleic acid source, such as RNA, e.g., cDNA.

In some embodiments, a sample that includes genomic nucleic acids to which the methods described herein may be applied may a biological sample such as a tissue sample, a biological fluid sample, or a cell sample, and processed fractions thereof. The sample may be from a mammal, for example, a human. A biological fluid sample includes, as non-limiting examples, blood, plasma, serum, sweat, tears, sputum, urine, ear flow, lymph, interstitial fluid, saliva, cerebrospinal fluid, ravages, bone marrow suspension, vaginal flow, transcervical lavage, brain fluid, ascites, milk, secretions of the respiratory, intestinal and genitourinary tracts, amniotic fluid and leukophoresis samples. In some embodiments, the source sample is a sample that is easily obtainable by non-invasive procedures, e.g., blood, plasma, serum, sweat, tears, sputum, urine, ear flow, or saliva. In some embodiments, the biological sample is a peripheral blood sample, or the plasma and serum fractions. In other embodiments, the biological sample is a swab or smear, a biopsy specimen, or a cell culture. In another embodiment, the sample is a mixture of two or more biological samples, e.g., a biological sample comprising two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In some embodiments, samples can be obtained from sources, including, but not limited to, samples from different individuals, different developmental stages of the same or different individuals, different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, or individuals with predisposition to a pathology, individuals with exposure to a pathogen such as an infectious disease agent (e.g., HIV), and individuals who are recipients of donor cells, tissues and/or organs. In one embodiment, the sample is a maternal sample that is obtained from a pregnant female, for example a pregnant human woman. In this instance, the sample can be analyzed using the methods described herein to provide a prenatal diagnosis of potential fetal disorders. Unless otherwise specified, a maternal sample includes a mixture of fetal and maternal DNA, e.g., cfDNA. In some embodiments, the maternal sample is a biological fluid sample, e.g., a blood sample. In other embodiments, the maternal sample is a purified cfDNA sample.

A sample can be an unprocessed biological sample, e.g., a whole blood sample. A source sample can be a partially processed biological sample, e.g., a blood sample that has been fractionated to provide a substantially cell-free plasma fraction. A source sample can be a biological sample containing purified nucleic acids, e.g., a sample of purified cfDNA derived from an essentially cell-free plasma sample. Processing of the samples can include freezing samples, e.g., tissue biopsy samples, fixing samples e.g. formalin-fixing, and embedding samples, e.g., paraffin-embedding. Partial processing of samples include sample fractionation, e.g., obtaining plasma fractions from blood samples, and other processing steps required for analyses of samples collected during routine clinical work, in the context of clinical trials, and/or scientific research. Additional processing steps can include steps for isolating and purifying sample nucleic acids. Further processing of purified samples includes, for example, steps for the requisite modification of sample nucleic acids in preparation for sequencing. Preferably, the sample is an unprocessed or a partially processed sample.

Samples can also be obtained from in vitro cultured tissues, cells, or other polynucleotide-containing sources. The cultured samples can be taken from sources including, but not limited to, cultures (e.g., tissue or cells) maintained in different media and/or conditions (e.g., pH, pressure, or temperature), maintained for different periods of time, and/or treated with different factors or reagents (e.g., a drug candidate, or a modulator), or mixed cultures of different types of tissue or cells.

Biological samples can be obtained from a variety of subjects, including but not limited to, mammals, e.g., humans, and other organisms, including, plants, or cells from the subjects, or microorganisms (e.g., bacteria, fungi).

Sample polynucleotides that can be prepared for sequencing and analyzed as described herein include genomic cellular DNA, cell-free DNA, mitochondrial DNA, RNA, and cDNA. Preparation of sequencing libraries for some NGS sequencing platforms require that the polynucleotides be of a specific range of fragment sizes, and require that large polynucleotides, e.g., cellular genomic DNA be fragmented. Fragmentation of polynucleotide molecules by mechanical means cleaves the DNA backbone at C—O, P—O and C—C results in a heterogeneous mix of blunt and 3'- and 5'-overhanging ends with broken C—O, P—O and/ C—C bonds (Alnemri and Litwack (1990) *J Biol Chem* 265:17323-17333; Richards and Boyer (1965) *J Mol Biol* 11:327-340), which need to be repaired for the subsequent enzymatic reactions, e.g., ligation of sequencing adaptors, that are required for preparing DNA for sequencing. Therefore, fragmentation of polynucleotides, e.g., cellular genomic DNA, may be required. Alternatively, fragmentation of cfDNA, which exists as fragments of <300 bases, may not necessary for generating a sequencing library using cfDNA samples.

Samples from which the target polynucleotides are derived can include multiple samples from the same individual, samples from different individuals, or combinations thereof. In some embodiments, a sample includes a plurality of polynucleotides from a single individual. In some embodiments, a sample includes a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, fluid sample, or organ sample derived therefrom (or cell cultures derived from any of these), including, for example, cultured cell lines, biopsy, blood sample, cheek swab, or fluid sample containing a cell (e.g., saliva). The subject may be an animal, including but not limited to, a cow, a pig, a mouse, a rat, a chicken, a cat, a dog, etc., and is usually a mammal, such as a human. In some embodiments, samples include DNA. In some embodiments, samples include genomic DNA. In some embodiments, samples include mitochondrial DNA, chloroplast DNA, plasmid DNA, bacterial artificial chromosomes, yeast artificial chromosomes, oligonucleotide tags, or combinations thereof. In some embodiments, the samples include DNA generated by amplification, such as by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can include sequences specific to one or more targets, random sequences, partially random sequences, and combinations thereof. Reaction conditions suitable for primer extension reactions are known in the art. In general, sample polynucleotides include any polynucleotide present in a sample, which may or may not include target polynucleotides. In some embodiments, a sample from a single individual is divided into multiple separate samples (e.g. 2, 3, 4, 5, 6, 7, 8, 9, 10, or more separate samples) that are subjected to the methods described herein independently, such as analysis in duplicate, triplicate, quadruplicate, or more.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent, with or without the use of an automated nucleic acid extractor; (2) stationary phase adsorption; and (3) salt-induced nucleic acid precipitation methods, such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads. In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the methods of the invention, such as to remove excess or unwanted reagents, reactants, or products. Methods for determining the amount and/or purity of nucleic acids in a sample are known in the art, and include absorbance (e.g., absorbance of light at 260 nm, 280 nm, and a ratio of these) and detection of a label (e.g., fluorescent dyes and intercalating agents, such as SYBR green, SYBR blue, DAPI, propidium iodine, Hoechst stain, SYBR gold, ethidium bromide).

In some embodiments, polynucleotides are fragmented into a population of fragmented polynucleotides of one or more specific size range(s). In some embodiments, the amount of sample polynucleotides subjected to fragmentation is about, less than about, or more than about 1 ng, 5 ng, 10 ng, 25 ng, 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 μg, or more. In some embodiments, fragments are generated from about, less than about, or more than about 1, 10, 100, 1000, 10000, 100000, 300000, 500000, or more genome-equivalents of starting DNA. Fragmentation may be accomplished by methods known in the art, including chemical, enzymatic, and mechanical fragmentation. In some embodiments, the fragments have an average or median length from about 10 to about 10,000 nucleotides. In some embodiments, the fragments have an average or median length from about 50 to about 2,000 nucleotides. In some embodiments, the fragments have an average or median length of about, less than about, more than about, or about 100 to about 2500, about 200 to about 1000, about 10 to about 800, about 10 to about 500, about 50 to about 500, about 50 to about 250, or about 50 to about 150 nucleotides (e.g., base pairs). In some embodiments, the fragments have an average or median length of about 300 to about 800 nucleotides (e.g., base pairs). In some embodiments, the fragments have an average or median length of about, less than about, or more than about 200, 300, 500, 600, 800, 1000, 1500 or more nucleotides (e.g., base pairs). In some embodiments, the fragmentation is accomplished mechanically, including subjecting sample polynucleotides to acoustic sonication. In some embodiments, the fragmentation includes treating the sample polynucleotides with one or more enzymes under conditions suitable for the one or more enzymes to generate double-stranded nucleic acid breaks. Examples of enzymes useful in the generation of polynucleotide fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of $Mg^{2+}$ and in the presence of $Mn^{2+}$. In some embodiments, fragmentation includes treating the sample polynucleotides with one or more restriction endonucleases. Fragmentation can produce fragments having 5' overhangs, 3' overhangs, blunt ends, or a combination thereof. In some embodiments, such as when fragmentation includes the use of one or more restriction endonucleases, cleavage of sample polynucleotides leaves overhangs having a predictable sequence. In some embodiments, the method includes the step of size selecting the fragments via standard methods such as column purification or isolation from an agarose gel. In some embodiments, the method includes determining the average and/or median fragment length after fragmentation. In some embodiments, samples having an average and/or median fragment length above a desired threshold are again subjected to fragmentation. In some embodiments, samples having an average and/or median fragment length below a desired threshold are discarded.

In some embodiments, the 5' and/or 3' end nucleotide sequences of fragmented polynucleotides are not modified prior to ligation with one or more adapter oligonucleotides. For example, fragmentation by a restriction endonuclease can be used to leave a predictable overhang, followed by ligation with one or more adapter oligonucleotides having an overhang complementary to the predictable overhang on a polynucleotide fragment. In another example, cleavage by an enzyme that leaves a predictable blunt end can be followed by ligation of blunt-ended polynucleotide fragments to adapter oligonucleotides that include a blunt end. In some embodiments, the fragmented polynucleotides are blunt-end polished (or "end repaired") to produce polynucleotide fragments having blunt ends, prior to being joined to adapters. Polynucleotide fragments having an overhang can be joined to one or more adapter oligonucleotides having a complementary overhang, such as in a ligation reaction. For example, a single adenine can be added to the 3' ends of end repaired polynucleotide fragments using a template independent polymerase, followed by ligation to one or more adapters each having an overhanging thymine at a 3' end. In some embodiments, adapter oligonucleotides can be joined to blunt end double-stranded DNA fragment molecules which have been modified by extension of the 3' end with one or more nucleotides followed by 5' phosphorylation. In some cases, extension of the 3' end may be performed with a polymerase such as for example Klenow polymerase or any other suitable polymerases known in the art, or by use of a terminal deoxynucleotide transferase, in the presence of one or more dNTPs in a suitable buffer containing magnesium. In some embodiments, target polynucleotides having blunt ends are joined to one or more adapters comprising a blunt end. Phosphorylation of 5' ends of fragmented polynucleotides may be performed for example with T4 polynucleotide kinase in a suitable buffer containing ATP and magnesium. The fragmented polynucleotides may optionally be treated to dephosphorylate 5' ends or 3' ends, for example, by using enzymes known in the art, such as phosphatases.

In some embodiments, the target sequence includes a variant, e.g., a causal genetic variant. A single causal genetic variant can be associated with more than one disease or trait. In some embodiments, a causal genetic variant can be associated with a Mendelian trait, a non-Mendelian trait, or both. Causal genetic variants can manifest as variations in a polynucleotide, such as at least about 1, 2, 3, 4, 5, 6, 7, 8, 9, 10, 20, 50, or more sequence differences (such as between a polynucleotide including the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants are known in the art. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease. Non-limiting examples of causal genetic variants are described in US2010/0022406, which is incorporated by reference in its entirety.

Causal genetic variants can be originally discovered by statistical and molecular genetic analyses of the genotypes and phenotypes of individuals, families, and populations. The causal genetic variants for Mendelian traits are typically identified in a two-stage process. In the first stage, families are identified in which multiple individuals who possess the trait are examined for genotype and phenotype. Genotype and phenotype data from these families is used to establish the statistical association between the presence of the Mendelian trait and the presence of a number of genetic markers. This association establishes a candidate region in which the causal genetic variant is likely to map. In a second stage, the causal genetic variant itself is identified. The second step typically entails sequencing the candidate region. More sophisticated, one-stage processes are possible with more advanced technologies which permit the direct identification of a causal genetic variant or the identification of smaller candidate regions. After one causal genetic variant for a trait is discovered, additional variants for the same trait can be discovered. For example, the gene associated with the trait can be sequenced in individuals who possess the trait or their relatives. Many causal genetic variants are cataloged in databases including the Online Mendelian Inheritance in Man (OMIM) and the Human Gene Mutation Database (HGMD).

A causal genetic variant may exist at any frequency within a specified population. In some embodiments, a causal genetic variant causes a trait having an incidence of no more than 1% a reference population. In another embodiment, a causal genetic variants causes a trait having an incidence of no more than $1/10,000$ in a reference population.

In some embodiments, a causal genetic variant which is associated with a disease or trait is a genetic variant, the presence of which increases the risk of having or developing the disease or trait by about, less than about, or more than about 1%, 5%, 10%, 15%, 20%, 25%, 30%, 40%, 50%, 60%, 70%, 80%, 90%, 100%, 200%, 300%, 400%, 500%, or more. In some embodiments, a causal genetic variant is a genetic variant the presence of which increases the risk of having or developing a disease or trait by about, less than about, or more than about 1-fold, 2-fold, 3-fold, 4-fold, 5-fold, 6-fold, 7-fold, 8-fold, 9-fold, 10-fold, 25-fold, 50-fold, 100-fold, 500-fold, 1000-fold, 10000-fold, or more. In some embodiments, a causal genetic variant is a genetic variant the presence of which increases the risk of having or developing a disease or trait by any statistically significant amount, such as an increase having a p-value of about or less than about 0.1, 0.05, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$, or smaller.

In some embodiments, a causal genetic variant has a different degree of association with a disease or trait between two or more different populations of individuals, such as between two or more human populations. In some embodiments, a causal genetic variant has a statistically significant association with a disease or trait only within one or more populations, such as one or more human populations. A human population can be a group of people sharing a common genetic inheritance, such as an ethnic group. A human population can be a haplotype population or group of haplotype populations. A human population can be a national group. A human population can be a demographic population such as those delineated by age, gender, and socioeconomic factors. Human populations can be historical populations. A population can consist of individuals distributed over a large geographic area such that individuals at extremes of the distribution may never meet one another. The individuals of a population can be geographically dispersed into discontinuous areas. Populations can be informative about biogeographical ancestry. Populations can also be defined by ancestry. Genetic studies can define populations. In some embodiments, a population may be based on ancestry and genetics. A sub-population may serve as a population for the purpose of identifying a causal genetic variant.

In some embodiments, a causal genetic variant is associated with a disease, such as a rare genetic disease. Examples of rare genetic diseases include, but are not limited to: 21-Hydroxylase Deficiency, ABCC8-Related Hyperinsulinism, ARSACS, Achondroplasia, Achromatopsia, Adenosine Monophosphate Deaminase 1, Agenesis of Corpus Callosum with Neuronopathy, Alkaptonuria, Alpha-1-Antitrypsin Deficiency, Alpha-Mannosidosis, Alpha-Sarcoglycanopathy, Alpha-Thalassemia, Alzheimers, Angiotensin II Receptor, Type I, Apolipoprotein E Genotyping, Argininosuccinicaciduria, Aspartylglycosaminuria, Ataxia with Vitamin E Deficiency, Ataxia-Telangiectasia, Autoimmune Polyendocrinopathy Syndrome Type 1, BRCA1 Hereditary Breast/Ovarian Cancer, BRCA2 Hereditary Breast/Ovarian Cancer, Bardet-Biedl Syndrome, Best Vitelliform Macular Dystrophy, Beta-Sarcoglycanopathy, Beta-Thalassemia, Biotinidase Deficiency, Blau Syndrome, Bloom Syndrome, CFTR-Related Disorders, CLN3-Related Neuronal Ceroid-Lipofuscinosis, CLN5-Related Neuronal Ceroid-Lipofuscinosis, CLN8-Related Neuronal Ceroid-Lipofuscinosis, Canavan Disease, Carnitine Palmitoyltransferase IA Deficiency, Carnitine Palmitoyltransferase II Deficiency, Cartilage-Hair Hypoplasia, Cerebral Cavernous Malformation, Choroideremia, Cohen Syndrome, Congenital Cataracts, Facial Dysmorphism, and Neuropathy, Congenital Disorder of Glycosylationla, Congenital Disorder of Glycosylation Ib, Congenital Finnish Nephrosis, Crohn Disease, Cystinosis, DFNA 9 (COCH), Diabetes and Hearing Loss, Early-Onset Primary Dystonia (DYT1), Epidermolysis Bullosa Junctional, Herlitz-Pearson Type, FANCC-Related Fanconi Anemia, FGFR1-Related Craniosynostosis, FGFR2-Related Craniosynostosis, FGFR3-Related Craniosynostosis, Factor V Leiden Thrombophilia, Factor V R2 Mutation Thrombophilia, Factor XI Deficiency, Factor XIII Deficiency, Familial Adenomatous Polyposis, Familial Dysautonomia, Familial Hypercholesterolemia Type B, Familial Mediterranean Fever, Free Sialic Acid Storage Disorders, Frontotemporal Dementia with Parkinsonism-17, Fumarase deficiency, GJB2-Related DFNA 3 Nonsyndromic Hearing Loss and Deafness, GJB2-Related DFNB 1 Nonsyndromic Hearing Loss and Deafness, GNE-Related Myopathies, Galactosemia, Gaucher Disease, Glucose-6-Phosphate Dehydrogenase Deficiency, Glutaricacidemia Type 1, Glycogen Storage Disease Type 1a, Glycogen Storage Disease Type Ib, Glycogen Storage Disease Type II, Glycogen Storage Disease Type III, Glycogen Storage Disease Type V, Gracile Syndrome, HFE-Associated Hereditary Hemochromatosis, Halder AIMs, Hemoglobin S Beta-Thalassemia, Hereditary Fructose Intolerance, Hereditary Pancreatitis, Hereditary Thymine-Uraciluria, Hexosaminidase A Deficiency, Hidrotic Ectodermal Dysplasia 2, Homocystinuria Caused by Cystathionine Beta-Synthase Deficiency, Hyperkalemic Periodic Paralysis Type 1, Hyperornithinemia-Hyperammonemia-Homocitrullinuria Syndrome, Hyperoxaluria, Primary, Type 1, Hyperoxaluria, Primary, Type 2, Hypochondroplasia, Hypokalemic Periodic Paralysis Type 1, Hypokalemic Periodic Paralysis Type 2, Hypophosphatasia, Infantile Myopathy and Lactic Acidosis (Fatal and Non-Fatal Forms), Isovaleric Acidemias, Krabbe Disease, LGMD2I, Leber Hereditary Optic Neuropathy, Leigh Syndrome, French-Canadian Type, Long Chain 3-Hydroxyacyl-CoA Dehydrogenase Deficiency, MELAS, MERRF, MTHFR Deficiency, MTHFR Thermolabile Variant, MTRNR1-Related Hearing Loss and Deafness, MTTS1-Related Hearing Loss and Deafness, MYH-Associated Polyposis, Maple Syrup Urine Disease Type 1A, Maple Syrup Urine Disease Type 1B, McCune-Albright Syndrome, Medium Chain Acyl-Coenzyme A Dehydrogenase Deficiency, Megalencephalic Leukoencephalopathy with Subcortical Cysts, Metachromatic Leukodystrophy, Mitochondrial Cardiomyopathy, Mitochondrial DNA-Associated Leigh Syndrome and NARP, Mucolipidosis IV, Mucopolysaccharidosis Type I, Mucopolysaccharidosis Type IIIA, Mucopolysaccharidosis Type VII, Multiple Endocrine Neoplasia Type 2, Muscle-Eye-Brain Disease, Nemaline Myopathy, Neurological phenotype, Niemann-Pick Disease Due to Sphingomyelinase Deficiency, Niemann-Pick Disease Type C1, Nijmegen Breakage Syndrome, PPT1-Related Neuronal Ceroid-Lipofuscinosis, PROP1-related pituitary hormone deficiency, Pallister-Hall Syndrome, Paramyotonia Congenita, Pendred Syndrome, Peroxisomal Bifunctional Enzyme Deficiency, Pervasive Developmental Disorders, Phenylalanine Hydroxylase Deficiency, Plasminogen Activator Inhibitor I, Polycystic Kidney Disease, Autosomal Recessive, Prothrombin G20210A Thrombophilia, Pseudovitamin D Deficiency Rickets, Pycnodysostosis, Retinitis Pigmentosa, Autosomal Recessive, Bothnia Type, Rett Syndrome, Rhizomelic Chondrodysplasia Punctata Type 1, Short Chain Acyl-CoA Dehydrogenase Deficiency, Shwachman-Diamond Syndrome, Sjogren-Larsson Syndrome, Smith-Lemli-Opitz Syndrome, Spastic Paraplegia 13, Sulfate Transporter-Related Osteochondrodysplasia, TFR2-Related Hereditary Hemochromatosis, TPP1-Related Neuronal Ceroid-Lipofuscinosis, Thanatophoric Dysplasia, Transthyretin Amyloidosis, Trifunctional Protein Deficiency, Tyrosine Hydroxylase-Deficient DRD, Tyrosinemia Type I, Wilson Disease, X-Linked Juvenile Retinoschisis and Zellweger Syndrome Spectrum.

In some embodiments, the target sequence includes a non-subject sequence. In general, a non-subject sequence corresponds to a polynucleotide derived from an organism other than the individual being tested, such as DNA or RNA from bacteria, archaea, viruses, protists, fungi, or other organism. A non-subject sequence may be indicative of the identity of an organism or class of organisms, and may further be indicative of a disease state, such as infection. An example of non-subject sequences useful in identifying an organism include, without limitation, ribosomal RNA (rRNA) sequences, such as 16s rRNA sequences (see, e.g., WO2010/151842). In some embodiments, non-subject sequences are analyzed instead of, or separately from causal genetic variants. In some embodiments, causal genetic variants and non-subject sequences are analyzed in parallel, such as in the same sample and/or in the same report.

Adaptors

Polynucleotide adaptors are provided for use in the methods disclosed herein. Adaptors herein include: (i) a double stranded region that is ligated to one end of the target nucleic acid duplex; and (ii) first and second single stranded regions. The first single stranded region includes at least a portion of a first sequencing primer binding sequence S2 and a 3' end. In some embodiments, the second single stranded region includes from 5' to 3', a 5' end, a first grafting sequence P5 for attachment to a flow cell, a first sample index sequence SI5, a molecular barcode sequence A, and at least a portion of a second sequencing primer binding site S1. In other embodiments, second single stranded region includes, from 5' to 3', a 5' end, a first grafting sequence P5 for attachment to a flow cell, a molecular barcode sequence A, a first sample index sequence SI5, and at least a portion of a second sequencing primer binding site S1. Adaptors that are ligated to the two ends of a target nucleic acid may contain molecular barcode sequences that are the same or different.

Figure 1:
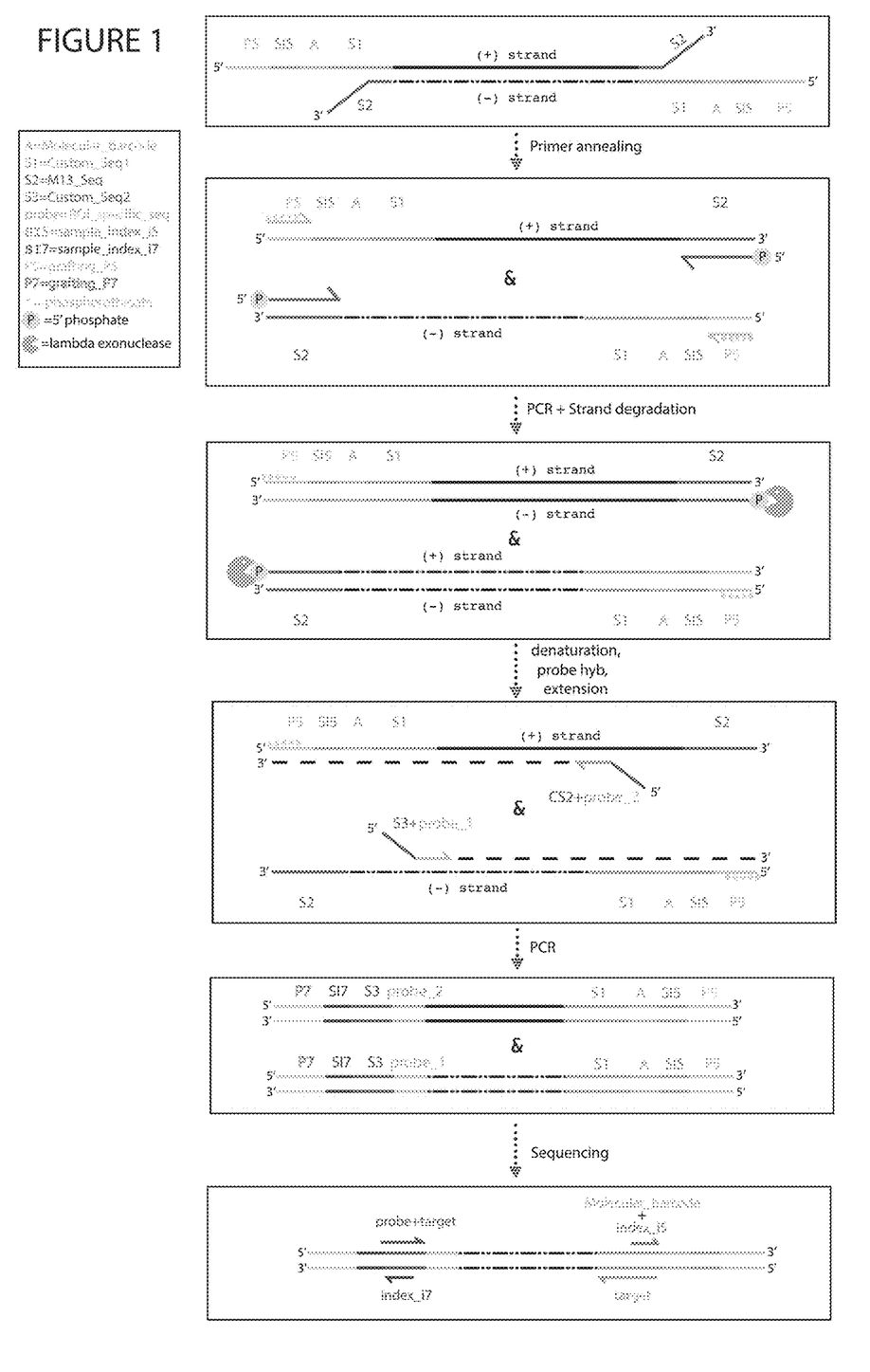
FIG. 1 schematically depicts an embodiment of a nucleic acid preparation and sequencing method as described herein.

In some embodiments, adaptors are Y-shaped, as shown in FIG. 1, with first and second single-stranded regions on separate polynucleotides.

A plurality of adaptors for use in the methods described herein may all contain the same molecular barcode sequence, or may include different barcode sequences.

Adapter oligonucleotides can include DNA, RNA, nucleotide analogues, non-canonical nucleotides, labeled nucleotides, modified nucleotides, or combinations thereof.

Adaptors may be ligated to first and second ends of a target nucleic acid duplex molecule in simultaneous or sequential reactions.

In some embodiments of the methods herein, fragmentation of polynucleotides is followed by ligation of adapter oligonucleotides to the fragmented polynucleotides. In some embodiments, an adapter is a mismatched adapter formed by annealing two partially complementary polynucleotide strands so as to provide, when the two strands are annealed, at least one double-stranded. A "double-stranded region" of the adapter is a short double-stranded region, typically including 5 or more consecutive base pairs, formed by annealing of the two partially complementary polynucleotide strands. This term simply refers to a double-stranded region of nucleic acid in which the two strands are annealed and does not imply any particular structural conformation. In some embodiments, a double-stranded region is about, less than about, or more than about 5, 10, 15, 20, 25, 30, or more nucleotides in length. In some embodiments, it is advantageous for the double-stranded region of a mismatched adapter to be as short as possible without loss of function. By "function" in this context is meant that the double-stranded region form a stable duplex under standard reaction conditions for an enzyme-catalyzed nucleic acid ligation reaction, which conditions are known to those skilled in the art (e.g., incubation at a temperature in the range of about 4° C. to about 25° C. in a ligation buffer appropriate for the enzyme), such that the two strands forming the adapter remain partially annealed during ligation of the adapter to a target molecule. It is not absolutely necessary for the double-stranded region to be stable under the conditions typically used in the annealing steps of primer extension or PCR reactions. The terminal double-stranded region is at the "ligatable" end of the adapter, i.e., the end that is joined to a target polynucleotide in a ligation reaction. The ligatable end of the adapter may be blunt or, in other embodiments, short 5' or 3' overhangs of one or more nucleotides may be present to facilitate/promote ligation. The 5' terminal nucleotide at the ligatable end of the adapter is typically phosphorylated to enable phosphodiester linkage to a 3' hydroxyl group on a sample polynucleotide. The term "unmatched region" refers to a region of the adapter wherein the sequences of two polynucleotide strands forming the adapter or a region of a single polynucleotide strand that forms the adaptor exhibit(s) a degree of non-complementarity such that polynucleotide sequences on the two strands or on the single strand are not capable of annealing to each other under standard annealing conditions for a primer extension or PCR reaction. The nucleotide sequences in the unmatched region may exhibit some degree of annealing under standard reaction conditions for an enzyme-catalyzed ligation reaction, provided that they revert to single stranded form under annealing conditions.

In some embodiments, the adapter oligonucleotides joined to target polynucleotides from one sample include sequences common to all adapter oligonucleotides and a barcode that is unique to the adapters joined to polynucleotides of that particular sample, such that the barcode sequence can be used to distinguish polynucleotides originating from one sample or adapter joining reaction from polynucleotides originating from another sample or adapter joining reaction.

In some embodiments, an adapter includes a 5' overhang, a 3' overhang, or both that is complementary to one or more target polynucleotide overhangs. Complementary overhangs can be one or more nucleotides in length, including but not limited to 1, 2, 3, 4, 5, 6, 7, 8, 9, 10, 11, 12, 13, 14, 15, or more nucleotides in length. In some embodiments, an adapter overhang is complementary to a target polynucleotide overhang produced by restriction endonuclease digestion. In some embodiments, an adapter overhang consists of an adenine or a thymine.

Figure 2:
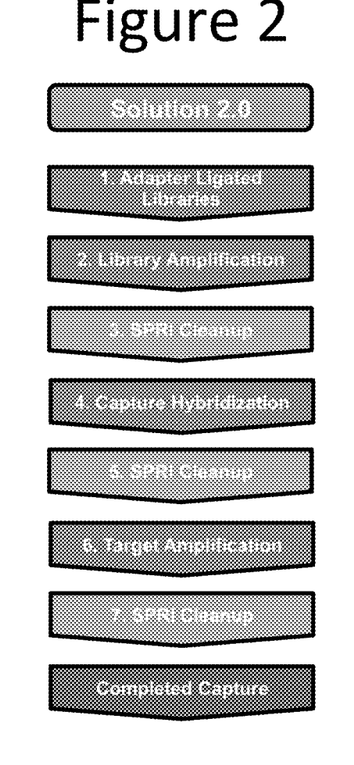
FIG. 2 illustrates an exemplary workflow of an embodiment of a method for preparing an adaptor ligated nucleic acid library for sequencing, as described herein.

In some embodiments, the sequencing adapter includes a constant 3'-overhang. The constant 3'-overhang is referred to as "constant" because the same 3'-overhang is used for each of the sequencing adapters in a composition. In some embodiments, the constant 3'-overhang can include adenine (A), thymine (T), guanine (G), cytosine (C), uracil (U), inosine (I), or any other natural or synthetic base. In some embodiments, the 3'-overhang includes a dinucleotide, such as a guanine-cytosine (GC) dinucleotide. The constant 3'-overhang can be ligated to the target nucleic acid molecule to be sequenced. FIG. 2 illustrates one exemplary embodiment of a sequencing adapter comprising a constant 3'-overhang. The molecular barcode is ligated adjacent to the nucleic acid molecule to be sequenced, except that it may be separated by the constant 3'-overhang (and/or its complementary base(s) that may be included in the complementary strand after ligation).

In some embodiments, the amount of target nucleic acid duplex molecules, e.g., fragmented polynucleotides subjected to adapter joining is about, less than about, or more than about 1 ng, 5 ng, 10 ng, 15 ng, 25 ng, 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 or more (e.g., a threshold amount). In some embodiments, the amount of fragmented polynucleotides is determined before proceeding with adapter joining, where adapter joining is not performed if the amount is below a threshold amount.

Methods for joining two polynucleotides are known in the art, and include without limitation, enzymatic and non-enzymatic (e.g., chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adapter oligonucleotide is joined to target nucleic acid duplex, e.g., a fragmented polynucleotide, by a ligase, for example a DNA ligase or RNA ligase. Multiple ligases, each having characterized reaction conditions, are known in the art, and include, without limitation $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Ligation can be between polynucleotides having hybridizable sequences, such as complementary overhangs. Ligation can also be between two blunt ends. Generally, a 5' phosphate is utilized in a ligation reaction. The 5' phosphate can be provided by the fragmented polynucleotide, the adapter oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction (i.e., an adapter end and a target nucleic acid duplex, e.g., fragmented polynucleotide, end) provide a 5' phosphate, such that two covalent linkages are made in joining the two ends. In some embodiments, 3' phosphates are removed prior to ligation.

Molecular Barcodes

The sequencing adapters described herein include a single-stranded molecular barcode with a predetermined or nondegenerate sequence. In some embodiments, the sequencing adapter includes one or more sample index(es).

Sequencing adapter compositions include a plurality of sequencing adapters, as described herein. The molecular barcodes in a plurality of sequencing adapters are diverse, although multiple copies of the same molecular barcode may be present in a composition including the plurality of sequencing adapters. For example, in some embodiments, the number of unique molecular barcodes in the plurality of sequencing adapters is between 2 and about 500, such as between about 10 and about 400, between about 20 and about 300, between about 50 and about 200, between about 10 and about 50, between about 50 and about 100, between about 75 and about 150, between about 100 and about 200, between about 200 and about 300, between about 300 and about 400, between about 400 and about 500, or about 24, about 48, about 96, about 192, or about 384.

In some embodiments, a molecular barcode in the plurality of sequencing adapters has an edit distance of 2 or more, 3 or more, 4 or more, 5 or more, 6 or more, 7 or more, or 8 or more from any other unique molecular barcode. Edit distance refers to the minimum number of single-base substitutions, single-base insertions, and/or single-base deletions that a pair of sequences must undergo to result in complete identity between the two sequences. For example, if the edit distance between a first molecular barcode and a second molecular barcode is 2, either the first molecular barcode must be mutated at least twice, the second molecular barcode must be mutated at least twice, or the first molecular barcode and the second molecular barcode must be mutated at least once each to result in identical sequences.

The molecular barcodes can be of any length, for example between about 2 and about 24 bases length. In some embodiments, the molecular barcodes are about 2, 3, 4, 5, 6, 7, 8, 9, 10, 11, 12, 13, 14, 15, 16, 17, 18, 19, 20, 21, 22, 23, or 24 bases in length. In some embodiments, the molecular barcodes are about 4 to about 15, or about 12 to about 15 based in length.

In some embodiments, the molecular barcodes are laser-color balanced. Laser-color balancing can help ensure that no single sequencing cycle is presented with only a single base when sequencing the molecular barcode. For example, some sequencing systems employ colored lasers to sequence nucleic acid molecules (for example, in some sequencing systems, a green laser is used to sequence G or T nucleotides, and a red laser is used to sequence A or C nucleotides). To avoid oversaturation of signal, resulting in sequencing quality loss, the molecular barcodes can be color balanced. In some embodiments, the molecular barcodes are laser-color balanced amongst the plurality of sequence adapters. For example, in some embodiments, the ratio of A/C to G/T nucleotides at any given position of the molecular barcode in the plurality of sequence adapters is between about 2:1 and about 1:2 (such as about 1:1) at the corresponding position relative to the shortest molecular barcode in the plurality of sequencing adapters. In some embodiments, the molecular barcodes are laser-color balanced within any given molecular barcode. For example, in some embodiments, the ratio of A/C to G/T nucleotides within any given molecular barcode is between about 2:1 and about 1:2 (such as about 1:1).

In some embodiments, the molecular barcodes are base-composition balanced. In some embodiments, the molecular barcodes are base-composition balanced amongst the plurality of sequence adapters. For example, in some embodiments, the proportion of adenine at any given position of the molecular barcode amongst the plurality of sequence adapters is between about 0.2 and about 0.4 (such as between about 0.2 and about 0.3, or about 0.25) at the corresponding position relative to the shortest molecular barcode in the plurality of sequencing adapters; the proportion of cytosine at any given position of the molecular barcodes is between about 0.2 and about 0.4 (such as between about 0.2 and about 0.3, or about 0.25) at the corresponding position relative to the shortest molecular barcode in the plurality of sequencing adapters; the proportion of thymine at any given position of the molecular barcodes is between about 0.2 and about 0.4 (such as between about 0.2 and about 0.3, or about 0.25) at the corresponding position relative to the shortest molecular barcode in the plurality of sequencing adapters; and the proportion of guanine at any given position of the molecular barcodes is between about 0.2 and about 0.4 (such as between about 0.2 and about 0.3, or about 0.25) at the corresponding position relative to the shortest molecular barcode in the plurality of sequencing adapters. In some embodiments, the molecular barcodes are base-composition balanced within the molecular barcode. For example, in some embodiments, the proportion of adenine within any given molecular barcodes is between about 0.2 and about 0.4 (such as between about 0.2 and about 0.3, or about 0.25); the proportion of cytosine within any given molecular barcodes is between about 0.2 and about 0.4 (such as between about 0.2 and about 0.3, or about 0.25); the proportion of thymidine within any given molecular barcodes is between about 0.2 and about 0.4 (such as between about 0.2 and about 0.3, or about 0.25); and the proportion of guanine within any given molecular barcodes is between about 0.2 and about 0.4 (such as between about 0.2 and about 0.3, or about 0.25).

In some embodiments, the proportion of any given nucleotide (e.g., A, T, C, or G) at any given position of the molecular barcode amongst the plurality of sequence adapters is between about 0.2 and about 0.3 (such as about 0.25).

Laser-color balancing and base-composition balancing within any given molecular barcode can be determined by counting the fraction of different nucleotide types within any molecular barcode. Base-composition balance need not be precisely balanced.

In some embodiments, the molecular barcodes include additional engineering features to enhance the sequencing quality. For example, in some embodiments, the molecular barcodes do not include homopolymer sequences (such as three or more consecutive, identical nucleotides; three or more consecutive, identical nucleotides; four or more consecutive, identical nucleotides; five or more consecutive, identical nucleotides; or six or more consecutive, identical nucleotides.

Preparation of Nucleic Acids for Sequencing

Methods are provided herein for preparing target nucleic acid duplex molecules for sequencing. A nonlimiting, exemplary illustration of the method is depicted in FIG. 1. In some embodiments, a library that contains a plurality of nucleic acid duplexes is prepared according to the methods described herein.

In one embodiment, the method includes:
(a) ligating an adaptor to each end of a target nucleic acid duplex, wherein the target nucleic acid duplex includes first and second nucleic acid strands that are complementary to one another, wherein each of the adaptors includes: (i) a double stranded region that is ligated to one end of the target nucleic acid duplex; and (ii) first and second single stranded regions, wherein the first single stranded region includes an amplification primer binding sequence S2 and a 3' end, and wherein the second single stranded region comprises, from 5' to 3', a 5' end, a first grafting sequence P5 for attachment to a flow cell, a first sample index sequence SI5, a molecular barcode A, and a first sequencing primer binding site S1, or wherein the second single stranded region comprises, from 5' to 3', a 5' end, a first grafting sequence P5 for attachment to a flow cell, a molecular barcode A, a first sample index sequence SI5, and a first sequencing primer binding site S1, wherein the molecular barcodes on the adaptors are the same or different;
(b) amplifying the ligated nucleic acid produced in (a) using a first amplification primer that includes a nucleic acid sequence that is complementary to the amplification primer binding sequence S2 and a second amplification primer that is complementary to at least a portion of the first grafting sequence P5, wherein the first amplification primer comprises a 5' phosphate group, and wherein the second amplification primer includes one or more nucleotide(s) at and/or near the 5' end including a modification to prevent nucleic acid strand degradation by an exonuclease enzyme;
(c) digesting the amplified nucleic acids produced in (b) with a 5'→3' exonuclease, thereby yielding single stranded nucleic acid products that include the sequence of either the first or second strand of the target nucleic acid duplex and the modified nucleotide(s) at and/or near the 5' end;
(d) hybridizing and extending a primer that includes: (i) a probe sequence that is complementary to a portion of the target nucleic acid sequence of the first and/or second strand; and (ii) a second sequencing primer binding sequence S3, thereby producing primer extension products that include the complement of the first grafting sequence P5 at the 3' end and second sequencing primer binding sequence S3 at 5' end; and
(e) amplifying the primer extension products, using: (i) a third amplification primer that includes, from 5' to 3', a second grafting sequence P7, a second sample index sequence SI7, and a sequence that is complementary to the second sequencing primer binding sequence S3; and (ii) a fourth amplification primer that includes the first grafting sequence P5, thereby producing amplified primer extension products for sequencing.

In some embodiments, the method may initiate at any of the above steps, i.e., step (a), (b), (c), (d), or (e).

In some embodiments, the nucleotide(s) at and/or near the 5' end of the second amplification primer to prevent degradation by an exonuclease enzyme in step (b) above include a phosphorothioate modification.

In some embodiments, the 5'→3' exonuclease used for digestion of amplified ligated target nucleic acid in step (c) above is a lambda exonuclease.

In some embodiments, step (d) above includes using two primers ("capture probes"), one with a probe sequence that hybridizes to the target sequence on the first strand and the other with a probe sequence that hybridizes to the target sequence on the second strand, both primers having the amplification primer binding sequence S3.

Sequencing

Methods for sequencing nucleic acids are provided. The methods include preparing a target nucleic acid duplex, or a plurality of target nucleic acid duplexes, for sequencing, employing methods described herein, and sequencing the products of the preparation methods, e.g., the amplified primer extension products of any of the preparation methods described herein.

In some embodiments, sequencing is performed in a flow cell that contains immobilized oligonucleotides that are complementary to the first and/or second grafting sequences.

In some embodiments, one or more first reads of a first strand of the target nucleic acid is performed, by sequencing with a primer that is complementary to the first sequencing primer binding site S1. In some embodiments, a second read of the second sample index SI7 is performed using a primer that is complementary to the second sequencing primer binding sequence S3. In some embodiments, a third read of the molecular barcode sequence A and the first sample index sequence SI5 is performed using a primer that is complementary to the first sequencing binding sequence S1. In some embodiments, a fourth read of the complement of the first strand target sequence is performed is performed using a primer with a sequence that is complementary to the second sequencing primer binding sequence S3. The first and second reads are performed on the amplified primer extension product that includes the target sequence, and the third and fourth reads are produced on the complementary amplified primer extension product that includes the complement of the target sequence.

In some embodiments, a set of first reads is compiled to construct a consensus sequence of the first strand of the target nucleic acid duplex, for example, based on sequence distance or alignment to a reference sequence. For example, a first strand consensus sequence may be constructed by: comparing first strand reads in a set of first strand reads; identifying and removing errors in the set of first strand reads; and constructing an error-corrected first strand consensus sequence. In some embodiments, one or more mutation(s) may be identified by comparison of the first strand consensus sequence, e.g., error-corrected first strand consensus sequence to a reference sequence.

In some embodiments, the complement of the first strand target sequenced is sequenced and a consensus sequence of the complement of the first strand target sequence is constructed. For example, a consensus sequence of the complement of the first strand target sequence may be constructed by: comparing fourth reads in a set of fourth reads; identifying and removing errors in the set of fourth reads; and constructing an error-corrected consensus sequence.

In some embodiments, the second strand target sequence is determined on the amplified primer extension product that includes the second strand target sequence, and its complementary amplified primer extension product, as described above for determination of the first strand target sequence. In some embodiments, a consensus sequence of the second strand of the target nucleic acid duplex is determined, and optionally a consensus sequence of the complement of the second strand target sequence, as described above for determination of the consensus sequence of the first strand target sequence and of the complement of the first strand target sequence.

Sequencing can be performed using any known sequencing method, such as single-molecule real-time sequencing, ion semiconductor sequencing, pyrosequencing, massively parallel signature sequencing, or sequencing-by-synthesis chemistry. An exemplary method of sequencing-by-synthesis chemistry is performed using an Illumina HiSeq 2500® sequencer or an Illumina Hi Seq 4000® sequencer.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for preparing a target nucleic acid duplex molecule for sequencing, comprising:
   (a) ligating an adaptor to each end of a target nucleic acid duplex,
      wherein the target nucleic acid duplex comprises first and second nucleic acid strands that are complementary to one another,
      wherein each of said adaptors comprises: (i) a double stranded region that is ligated to one end of the target nucleic acid duplex; and (ii) first and second single stranded regions,
      wherein the first single stranded region comprises an amplification primer binding sequence S2 and a 3' end, and
      wherein the second single stranded region comprises, from 5' to 3', a 5' end, a first grafting sequence P5 for attachment to a flow cell, a first sample index sequence SI5, a molecular barcode A, and a first sequencing primer binding site S1, or wherein the second single stranded region comprises, from 5' to 3', a 5' end, a first grafting sequence P5 for attachment to a flow cell, a molecular barcode A, a first sample index sequence SI5, and a first sequencing primer binding site S1,
      wherein the molecular barcodes on the adaptors are the same or different;
   (b) amplifying the ligated nucleic acid produced in (a) using a first amplification primer that comprises a nucleic acid sequence that is complementary to the amplification primer binding sequence S2 and a second amplification primer that is complementary to at least a portion of the first grafting sequence P5,
      wherein the first amplification primer comprises a 5' phosphate group, and
      wherein the second amplification primer comprises one or more nucleotide(s) at or near the 5' end comprising a modification to prevent nucleic acid strand degradation by an exonuclease enzyme;
   (c) digesting the amplified nucleic acids produced in (b) with a 5'→3' exonuclease, thereby yielding single stranded nucleic acid products that comprise the sequence of either the first or second strand of the target nucleic acid duplex and said modified nucleotide(s) at and/or near the 5' end;
   (d) hybridizing and extending a primer that comprises: (i) a probe sequence that is complementary to a portion of the target nucleic acid sequence of the first or second strand; and (ii) a second sequencing primer binding sequence S3, thereby producing primer extension products that comprise the first grafting sequence P5 at the 3' end and second sequencing primer binding sequence S3 at the 5' end; and
   (e) amplifying the primer extension products, using: (i) a third amplification primer that comprises, from 5' to 3', a second grafting sequence P7, a second sample index sequence SI7, and a sequence that is complementary to the second sequencing binding sequence S3; and (ii) a fourth amplification primer that comprises a sequence that is complementary to the first grafting sequence P5, thereby producing amplified primer extension products and their complements for sequencing.

2. A method according to claim 1, wherein prior to step (a), DNA in a sample is fragmented into a population of about 1 ng or more of fragmented DNA that comprises the target nucleic acid duplex.

3. A method according to claim 1, wherein prior to step (a), DNA in a sample is fragmented into a population of about 5 ng or more of fragmented DNA that comprises the target nucleic acid duplex.

4. A method according to claim 2, wherein the amplified nucleic acid product of step (b) is about 200 ng or more of amplified ligated nucleic acid.

5. A method according to claim 1, wherein the modified nucleotide(s) in the second amplification primer in step (b) comprise a 5' phosphorothioate group.

6. A method according to claim 5, wherein the second amplification primer comprises five or more phosphorothioate modified nucleotides at or near the 5' end of the primer.

7. A method according to claim 1, wherein the exonuclease in step (c) is a double-stranded exonuclease.

8. A method according to claim 7, wherein the exonuclease is a lambda exonuclease.

9. A method according to claim 1, wherein the molecular barcode in the second single-stranded region of the adaptor is about 5 to about 15 nucleotides in length.

10. A method according to claim 1, wherein said amplifying in step (b) comprises polymerase chain reaction (PCR) or a linear amplification method.

11. A method according to claim 1, wherein said amplifying in step (e) comprises PCR or a linear amplification method.

12. A method according to claim 1, comprising repeating step (d) with a plurality of different probes, in different reaction mixtures, to produce a plurality of primer extension products that will provide different start points for sequencing of the target nucleic acid sequence.

13. A method according to claim 1, wherein the target nucleic acid duplex comprises cell-free DNA.

14. A method according to claim 13, wherein the cell-free DNA comprise cell-free tumor DNA or cell-free fetal DNA.

15. A method according to claim 1, wherein, prior to step (a), the target nucleic acid duplex is enriched from a nucleic acid library.

16. A method according to claim 15, wherein the target nucleic acid duplex is enriched using a set of capture probes for a region of interest.

17. A method for sequencing a target nucleic acid, comprising preparing a target nucleic acid duplex for sequencing according to claim 1, and sequencing the product of step (e).

18. A method according to claim 17, wherein said sequencing occurs in a flow cell that comprises oligonucleotides that are complementary to and to which the first and/or second grafting sequence hybridizes.

19. A method according to claim 18, comprising performing a first read of the first strand target sequence using a primer with a sequence that is complementary to the first sequencing primer binding site on the amplified primer extension product that includes the first strand target sequence.

20. A method according to claim 19, comprising performing a second read to read the second sample index sequence and performing a third read to read the molecular barcode and first sample index sequences.

21. A method according to claim 20, comprising performing a fourth read of the probe and first strand target sequences using a primer with a sequence that is complementary to the second sequencing primer binding sequence on the amplified primer extension product that comprises the complement of the first strand target sequence.

22. A method according to claim 17, comprising compiling a set of first reads to construct a consensus sequence of the first strand of the target nucleic acid duplex.

23. A method according to claim 22, wherein the set of first strand reads is compiled based on sequence distance or alignment to a reference sequence.

24. A method according to claim 22, wherein constructing the first strand consensus sequence comprises:
comparing the first strand reads in the set of first strand reads;
identifying and removing errors in the set of first strand reads; and
constructing an error-corrected first strand consensus sequence.

25. A method according to claim 24, comprising identifying a mutation by comparison of the error-corrected consensus sequence to a reference sequence.

26. A method for preparing a nucleic acid sequencing library, comprising preparing a plurality of target DNA duplexes for sequencing in a method according to claim 1.

* * * * *